United States Patent [19]

Guczoghy et al.

[11] 4,051,156

[45] Sept. 27, 1977

[54] N-(TRIARYL-METHYL)-AMIDINES, PROCESS FOR THE PREPARATION THEREOF AND COMPOSITIONS CONTAINING THE SAME

[75] Inventors: Lajos Guczoghy; Todor Pfliegel; Maria Puklics; Laszlo Institoris; Jeno Seres, all of Budapest, Hungary

[73] Assignee: Chinoin Gyogyszer es Vegyeszeti Termekek Gyara Rt, Budapest, Hungary

[21] Appl. No.: 376,445

[22] Filed: July 5, 1973

[30] Foreign Application Priority Data

July 5, 1972 Hungary .................................... 1250

[51] Int. Cl.[2] ............................................. C09B 11/10
[52] U.S. Cl. ............................................... 260/393
[58] Field of Search .................................... 260/393

[56] References Cited

U.S. PATENT DOCUMENTS

| 1,149,575 | 8/1915 | Gartner et al. | 260/393 |
| 3,418,128 | 12/1968 | Huett | 260/393 X |

*Primary Examiner*—Paul F. Shaver
*Attorney, Agent, or Firm*—Karl F. Ross

[57] ABSTRACT

A compound selected from the group which consists of the amidine of formula

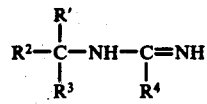

and the phytotoxically acceptable addition salts, hemihydrates and hydrates thereof, $R^1$, $R^2$ and $R^3$ being phenyl or a phenyl group substituted with chlorine, bromine, iodine or fluorine, alkoxy having 1–4 carbon atoms or alkyl having 1 to 4 carbon atoms;

$R^4$ being methyl.

8 Claims, No Drawings

N-(TRIARYL-METHYL)-AMIDINES, PROCESS FOR THE PREPARATION THEREOF AND COMPOSITIONS CONTAINING THE SAME

This invention relates to new N-(triaryl-methyl)-amidine derivatives, a process for the preparation thereof, and pharmaceutical, fungicidal and herbicidal compositions containing the same.

In the literature several biologically active compounds are known, which contain a N-(triaryl-methyl)-radical. (The term "aryl group" is used in the broad sense and relates to both aryl and heteroaryl groups.) Such known compounds are the (bis-phenyl)-(2-chloro-phenyl)-1-imidazolyl-methane (Bay b 5097, Subs. Med. 21 (4) 121, 1969., Hungarian Patent Application Ser. No. Ba-2105) and N-tritylmorpholine (Frescon, Belgian Patent Specification No. 625 441), which is a molluscicidal agent. The compound Bay b 5097 may be used in human therapy and also as systemic fungicide, the daily oral dose thereof being about 40 mg/kg. The preparation of this compound is however expensive.

The present invention relates to new amidines of the formula (I)

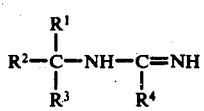

phytitoxically acceptable acid addition salts, and hemi- and monohydrates thereof (wherein $R^1$, $R^2$, and $R^3$ are identical or different aryl or heteroaryl groups, which may be optionally substituted;

$R^4$ is alkyl, aralkyl, aryl or heteroaryl).

The aryl group relates preferably to a phenyl group, which may be optionally substituted by one or more substituents. The preferred substituents of the phenyl group are halogen atoms (e.g. chlorine, bromine, iodine and fluorine) alkoxy (e.g. lower alkoxy having 1–4 carbon atoms, preferably methoxy or ethoxy) and alkyl (e.g. lower alkyl having 1–4 carbon atoms, such as methyl or ethyl group).

Particularly preferable representatives of the compounds of the formula (I) are the following derivatives:
N-[bis-phenyl-(2-methoxy-5-chloro-phenyl)-methyl]-acetamidine; N-trityl-acetamidine;
N-[bis-phenyl-(2-chloro-phenyl)-methyl]-acetamidine; and salts, hemi-hydrates and hydrates thereof.

According to a further feature of the present invention, there is provided a process for the preparation of compounds of the formula (I)

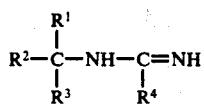

salts, hydrates and hemi-hydrates thereof (wherein $R^1$, $R^2$, $R^3$, and $R^4$ have the same meaning as stated above), which comprises a. Reacting a compound of the formula (II)

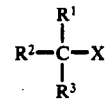

with a compound of the formula (III)

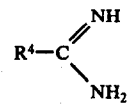

(wherein $R^1$, $R^2$ and $R^3$ have the same meaning as stated above; X stands for a halogen atom, and $R^4$ stands for an alkyl, aralkyl, aryl or heteroaryl group), or b. reacting a compound of the formula (IV)

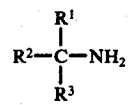

with a compound of the formula (V)

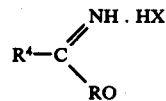

(wherein $R^1$, $R^2$, $R^3$ and $R^4$ and X have the same meaning as stated above; R stands for an optionally substituted alkyl, aralkyl or aryl group) and if desired, converting a compound of the formula (I) thus obtained into a phytitoxically acceptable salt, or hydrate or hemihydrate thereof.

The triaryl-methanols used as starting material may be prepared by one of the usual synthesis (e.g. Org. Synth. Coll. Vol. III. 389) and thereafter reacted with a double molar amount of acetyl halide under heating to boiling to give the corresponding halide of the formula (II); it is necessary to protect these compounds carefully from moisture, since they rapidly decompose.

The halides thus obtained are reacted with amidines of the formula (III). The amidines may be set free from the corresponding halide salts thereof by means of heating to boiling in an inert solvent with an alcoholate and the base thus obtained is introduced to further reaction without isolation.

According to method a/ of the process of the present invention the compounds of the formulae (II) and (III) are heated in the presence of an inert organic solvent, preferably benzene. After the termination of the reaction the mixture is cooled and the hydrogen halide (preferably in alcoholic solution) is added, whereupon the reaction mixture is evaporated or — if the product obtained is soluble — in the solvent used — the solvent is distilled off.

According to method b/ of our process to a solution of an imino ether-salt of the formula (V) in a cold inert organic solvent (preferably toluene) a primary amine of the formula (IV) is added, the reaction mixture is warmed at the beginning and later heated to boiling and the amidines are isolated.

The corresponding hemi-hydrate or monohydrate may be prepared by recystallization from water.

The formation of the phytetoxically acceptable acid addition salts from the bases is carried out by known methods by reacting with the corresponding acid.

According to a further feature of the present invention there are provided pharmaceutical compositions for use in human therapy and compositions for use in agriculture containing as active ingredient a compound of the formula (I) or a salt hydrate or hemi-hydrate thereof, in admixture with suitable inert solid or liquid carriers or diluents. Thus N-[bis-phenyl-(2-methoxy-5-chloro-phenyl)-methyl]-acetamidine and its salts prossess outstanding fungicidal and herbicidal properties and also shows antiviral and anticancerogenic effect. They are active against gram positive bacteria, pathogenic fungi and pathogenic microbacteria.

The compounds of the formula (I) and salts thereof may be used in therapy in the form of pharmaceutical compositions, which contain the active ingredient in admixture with inert non-toxic, pharmaceutically acceptable organic or inorganic carriers. The compositions may be finished e.g. in solid (e.g. tablets, film coated tablets, dragees, capsules) or liquid (e.g. suspension, solution or emulsion) form. As solvent one may use talc, starch, gelatine, glycols and other usual substances. The compositions may optionally contain other auxiliary agents (e.g. emulsifying or suspending agents) and/or further therapeutically active substances.

Plant protecting compositions containing a compound of the formula (I) as active ingredient may be prepared by several known methods and may be finished in the form of solutions, emulsions, suspensions or powders. The active ingredient is generally diluted with carriers and/or other auxiliary agents. As carrier china clay, wood flour, synthetic silicic acid, calcium silicate and other solid, inert materials may be used. As liquid carrier xylene, benzene, paraffines (e.g. mineral oil fractions) and alcohols may be used.

Further details of our invention are to be found in the Examples without limiting the scope of the present invention to the Examples.

EXAMPLE 1

Into an apparatus equipped with a stirrer 18 ml. of anhydrous methanol are introduced under anhydrous nitrogen, whereupon 1.03 g. (45 millimoles) of sodium is added. After the dissolution of the sodium 4.25 g. (45 millimoles) of acetamidine-hydrochloride are added to the solution and after the dropwise addition of 20 ml of benzene the mixture is warmed. The distilled solvent is replaced by anhydrous benzene until the internal temperature reaches 80° C. The mixture is cooled to 65° C, whereupon a solution of bis-phenyl-(2-methoxy-5-chloro)-phenyl-methylchloride and 20 ml of benzene is added. The reaction mixture is heated to boiling for half an hour, then cooled to 40° C and acidified with 6.6 ml (24 millimoles) of 3.65 n ethanolic hydrochloric acid to the pH-value of 3.

The methanol is distilled off with the aid of benzene, whereupon the mixture is cooled to 55° C, filtered in vacuo, filtrate is washed three-times with 10 ml. of anhydrous benzene each and dried in vacuo (10,7 g.). The product is heated three-times with 40 ml. of dichloroethane each, and filtered in vacuo. The dry weight of the residual sodium chloride and acetamidine hydrochloride amounts to 4,7 g. The acetamidine hydrochloride may be recovered by means of extraction with alcohol. The filtrate is cooled and placed in a refrigerator overnight. The precipitated N-[bis-phenyl-(2-methoxy-5-chloro-phenyl)-methyl]-acetamidinium-chloride crystals are filtered, washed three-times with 5 ml. of dichloro-ethane each, and dried in vacuo. Yield 79%, 5.68 g. (14.2 millimoles) mp.: 224°-230° C. According to elemental analysis the product is contaminated with a very small amount of water and dichloroethane.

EXAMPLE 2

5.68 g. of the product obtained according to Example 1 are dissolved in 120 ml. of water, the solution is clarified with 0.5 g. of activated charcoal and evaporated in vacuo to a volume of about 15 ml. The crystals precipitated on cooling are filtered and dried in vacuo. Thus 3.91 g. (9.32 millimoles) of N-[bis-phenyl-(2-methoxy5-chloro-phenyl)-methyl]-acetamidinium-chloride-monohydrate are obtained. Mp.: 155°-165° C. Yield 52%. The product is very sensitive to the moisture content of air.
Elemental analysis: Calculated %: C 63 H 5.08 Cl 8.4 eCl 16.9 N 6.68; Found %: C 62.2 H 5.95 Cl 8.44 eCl 16.71 N 6.16.

EXAMPLE 3

The N-[bis-phenyl-(2-methoxy-5-chloro-phenyl)-methyl]-3,4-dimethoxy benzyl amidinium-chloride-monohydrate is prepared in an analogous manner to the process described in Example 1. The substance is however insoluble in benzene, therefore after the filtration of sodium chloride and 3,4-dimethoxy-benzylamidine-hydrochloride the anhydrous molecule is obtained by evaporating the benzene extract. On crystallizing the product from water as described in Example 2, a substance, which melts at 142°-148° C and contains 1 mole of crystal water, is obtained.
Elementary analysis: Calculated %: C 64.86 H 5.8 Cl 12.76 N 5.04; Found %: C 64.6 H 6.1 Cl 12.67 N 4.76.

EXAMPLE 4

The N-trityl-acetamidinium-chloride-hemi-hydrate is prepared in an analogous manner to the process described in Examples 1 and 3 from trityl-chloride and acetamidine. Mp.: 138°-145° C.
Elementary analysis: Calculated %: C 72.9 H 6.4 Cl 10.25 N 8.09 Found %: C 72.8 H 5.99 Cl -10.82 N 7.98

EXAMPLE 5

In an analoguous manner to the process described in the preceeding Examples from bis-phenyl-(2-chlorophenyl)methylchloride and acetamidine the N-[bis-phenyl-(2-chlorophenyl)-methyl]-acetamidinium-chloride-monohydrate is obtained. Mp.: 150°-155° C.
Elementary analysis: Calculated %: C 66.32 H 5.56 Cl 9.32 eCl 18.64 N 7.36 Found %: C 66.11 H 5.5 Cl 9.85 eCl 18.78 N 7.29

EXAMPLE 6

3.3 g. of crude N-[bis-phenyl-(2-methoxy-5-chlorophenyl)-methyl]-acetamidinium-hydrochloride are dissolved in 100 ml. of water and the solution is made alkaline with ammoniumhydroxide. The precipitated product is filtered and wahed chloride-free with water. The moist weight of the product amounts to 3.12 g. After drying in vacuo 2.12 g. of dry N-[bis-phenyl-(2-methoxy-5-chlorophenyl)-methyl]-acetamidine are obtained. Mp.: 143°-145° C.
Microanalysis:
$C_{72.5}$ 71.99

$H_{5.76}$: 5.65
$N_{7.7}$: 7.43
$Cl_{9.75}$: 9.89

What we claim is:

1. An amidine derivative of the formula:

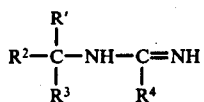

wherein
R', $R^2$, and $R^3$ are identical or different aryl groups; and
$R^4$ is alkyl, aralkyl or aryl.

2. A compound as defined in claim 1 wherein R', $R^2$, and $R^3$ are phenyl, halogenophenyl, alkoxyphenyl groups or phenyl groups substituted by a halogen atom and an alkoxy group.

3. A compound selected from the group which consists of N-[bis-phenyl-(2-methoxy-5-chloro-phenyl)-methyl]-acetamidine;
N-trityl-acetamidinium-chloride;
N-[bis-phenyl-(2-chloro-phenyl)-methyl]-acetamidine, and salts, hemihydrates and hydrates thereof.

4. The compound defined in calim 1 wherein at least one of R', $R^2$ and $R^3$ is 2-methoxy-5-chlorophenyl.

5. The compound defined in claim 1 wherein R', $R^2$ and $R^3$ are trityl groups.

6. The compound defined in claim 1 wherein one of R', $R^2$ and $R^3$ is 2-chlorophenyl.

7. A process for the preparation of a compound of the formula

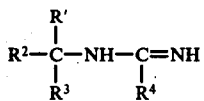

wherein
R', $R^2$, $R^3$ are aryl and $R^4$ is alkyl, aralkyl or aryl which comprises
a. reacting a compound of the formula

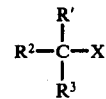

with a compound of the formula

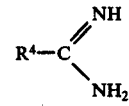

wherein
X is a halogen atom and $R^4$ is alkyl, aralkyl or aryl or
b. reacting a compound of the formula

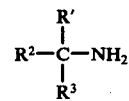

with a compound of the formula

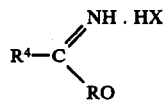

wherein
R is alkyl, aralkyl, or aryl.

8. The process according to claim 7 which comprises carrying out the reaction in the presence of an inert, organic solvent.

* * * * *